United States Patent
Oppenheimer et al.

(10) Patent No.: US 9,376,390 B2
(45) Date of Patent: *Jun. 28, 2016

(54) METHODS OF ISOLATING (4-CHLORO-2-FLUORO-3-SUBSTITUTED-PHENYL)BORONATES AND METHODS OF USING THE SAME

(71) Applicant: Dow AgroSciences LLC, Indianapolis, IN (US)

(72) Inventors: Jossian Oppenheimer, Midland, MI (US); Catherine A. Menning, Midland, MI (US); Daniel Randolph Henton, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/711,540

(22) Filed: May 13, 2015

(65) Prior Publication Data
US 2015/0239843 A1    Aug. 27, 2015

Related U.S. Application Data

(62) Division of application No. 13/729,580, filed on Dec. 28, 2012, now Pat. No. 9,045,502.

(60) Provisional application No. 61/582,175, filed on Dec. 30, 2011.

(51) Int. Cl.
*C07D 213/803* (2006.01)
*C07F 5/02* (2006.01)
*C07D 213/807* (2006.01)

(52) U.S. Cl.
CPC ........ *C07D 213/803* (2013.01); *C07D 213/807* (2013.01); *C07F 5/025* (2013.01)

(58) Field of Classification Search
None
See application file for complete search history.

(56) References Cited

U.S. PATENT DOCUMENTS

| | | | |
|---|---|---|---|
| 7,915,200 B2 | 3/2011 | Epp et al. | |
| 7,964,758 B2 | 6/2011 | Matoba et al. | |
| 2003/0114311 A1* | 6/2003 | Balko et al. | 504/235 |
| 2007/0179060 A1* | 8/2007 | Balko et al. | 504/193 |
| 2008/0045734 A1* | 2/2008 | Balko et al. | 556/81 |
| 2009/0182168 A1 | 7/2009 | Arndt et al. | |
| 2015/0133301 A1* | 5/2015 | Epp et al. | 546/290 |

FOREIGN PATENT DOCUMENTS

| | | |
|---|---|---|
| EP | 2181098 | 5/2010 |
| EP | 2332914 | 6/2011 |
| WO | 2007082076 | 7/2007 |
| WO | 2007082098 | 7/2007 |
| WO | 2009023438 | 2/2009 |
| WO | 2009029735 | 3/2009 |
| WO | 2009089310 | 7/2009 |

OTHER PUBLICATIONS

International Search Report and Written Opinion for International Application No. PCT/US2012/071920, dated Apr. 10, 2013.
Cammidge et al., "Application of the Suzuki Reaction as the Key Step in the Synthesis of a Novel Atropisomeric Biphenyl Derivative for Use as a Liquid Crystal Dopant", Journal of Organic Chemistry, May 15, 2003, vol. 68, No. 17, pp. 6832-6835.
Zhichkin et al., "Preparation of 2-Fluro-3-aminophenylboronates via Directed ortho-Metalation," Synthesis 2011, pp. 1604-1608, No. 10.

* cited by examiner

*Primary Examiner* — Karl J Puttlitz
(74) *Attorney, Agent, or Firm* — Michael J. Terapane; Magleby Cataxinos & Greenwood

(57) ABSTRACT

Methods of isolating a 4-chloro-2-fluoro-3-substituted-phenylboronate include adding carbon dioxide gas or carbon dioxide solid (dry ice) to a solution comprising a 4-chloro-2-fluoro-3-substituted-phenylboronate, an inert organic solvent, and at least one lithium salt to react the at least one lithium salt with the carbon dioxide gas or carbon dioxide solid (dry ice) and form a mixture comprising the 4-chloro-2-fluoro-3-substituted-phenylboronate, the inert organic solvent, and a precipitated solid. The precipitated solid may be removed from the mixture. Methods of using 4-chloro-2-fluoro-3-substituted-phenylboronates to produce methyl-4-amino-3-chloro-6-(4-chloro-2-fluoro-3-substituted-phenyl)pyridine-2-carboxylates are also disclosed. A 4-chloro-2-fluoro-3-substituted-phenylboronate produced by one of the methods of isolating a 4-chloro-2-fluoro-3-substituted-phenylboronate is also disclosed, wherein the 4-chloro-2-fluoro-3-substituted-phenylboronate may be obtained at a yield of greater than or equal to about 90%.

5 Claims, No Drawings

METHODS OF ISOLATING (4-CHLORO-2-FLUORO-3-SUBSTITUTED-PHENYL)BORONATES AND METHODS OF USING THE SAME

CROSS-REFERENCE TO RELATED APPLICATIONS

This application is a divisional of U.S. patent application Ser. No. 13/729,580, filed Dec. 28, 2012, pending, which claims the benefit of U.S. Provisional Patent Application Ser. No. 61/582,175, filed Dec. 30, 2011, the disclosure of each of which is hereby incorporated herein in its entirety by this reference.

TECHNICAL FIELD

Embodiments of the present disclosure relate to methods of isolating 4-chloro-2-fluoro-3-substituted-phenylboronates, and to methods of using 4-chloro-2-fluoro-3-substituted-phenylboronates. Embodiments of the present disclosure also relate to methods of isolating dimethyl 4-chloro-2-fluoro-3-methoxyphenylboronate (PBA-diMe), and to methods of using the same.

BACKGROUND 4-chloro-2-fluoro-3-methoxyphenylboronic acid (PBA), and 2-(4-chloro-2-fluoro-3-methoxyphenyl)-1,3,2-dioxaborinane (PBE) are useful in the synthesis of 6-(poly-substituted aryl)-4-aminopyridine-2-carboxylates and 2-(poly-substituted aryl)-6-amino-4-pyrimidinecarboxylic acids, which are useful as herbicide intermediates.

PBA may be synthesized by reacting 2-chloro-6-fluoroanisole with n-butyl lithium and trimethyl borate B(OMe)$_3$, adding an aqueous base to the reaction mixture, diluting the reaction mixture with acetonitrile, and acidifying the reaction mixture with hydrochloric acid. PBA may be esterified using 1,3-propanediol to form PBE.

It would be desirable to be able to reduce unit operations by isolating and using a precursor to either PBA or another 4-chloro-2-fluoro-3-substituted-phenylboronic acid to efficiently synthesize 6-(poly-substituted aryl)-4-aminopyridine-2-carboxylates and 2-(poly-substituted aryl)-6-amino-4-pyrimidinecarboxylic acids.

BRIEF SUMMARY

An embodiment of the present disclosure includes a method of isolating a 4-chloro-2-fluoro-3-substituted-phenylboronate that comprises adding carbon dioxide gas or carbon dioxide solid (dry ice) to a solution comprising a 4-chloro-2-fluoro-3-substituted-phenylboronate, an inert organic solvent, and at least one lithium salt to react the at least one lithium salt with the carbon dioxide gas and form a mixture comprising the 4-chloro-2-fluoro-3-substituted-phenylboronate, the inert organic solvent, and a precipitated solid. The precipitated solid may be removed from the mixture.

Another embodiment of the present disclosure includes a method of synthesizing and isolating dimethyl 4-chloro-2-fluoro-3-methoxylphenylboronate that comprises contacting a solution comprising 2-chloro-6-fluoroanisole and 1,2-dimethoxyethane with n-butyl lithium to form a reaction mixture comprising 6-chloro-2-fluoro-3-lithioanisole and the 1,2-dimethoxyethane. The reaction mixture may be contacted with trimethyl borate to form a salinated phenyl boronate solution comprising dimethyl 4-chloro-2-fluoro-3-methoxyphenylboronate, the 1,2-dimethoxyethane, and at least one lithium salt. Carbon dioxide gas or carbon dioxide solid (dry ice) may be introduced to the salinated phenyl boronate solution to form a mixture comprising the dimethyl 4-chloro-2-fluoro-3-methoxyphenylboronate, the 1,2-dimethoxyethane, and lithium methyl carbonate. The lithium methyl carbonate may be separated to form a desalinated phenyl boronate solution comprising the dimethyl 4-chloro-2-fluoro-3-methoxyphenylboronate and the 1,2-dimethoxyethane.

Yet another embodiment of the present disclosure includes a method of using a 4-chloro-2-fluoro-3-substituted-phenylboronate comprising reacting the 4-chloro-2-fluoro-3-substituted-phenylboronate with a 4-acetamido-3,6-dichloropicolinate, e.g., methyl 4-acetylamino-3,6-dichloropyridine-2-carboxylate, to produce a 6-(4-chloro-2-fluoro-3-substituted-phenyl)-4-aminopicolinate, e.g., methyl 4-amino-3-chloro-6-(4-chloro-2-fluoro-3-methoxyphenyl)pyridine-2-carboxylate.

A particular embodiment of the present disclosure includes a 4-chloro-2-fluoro-3-substituted-phenylboronate produced by a process that comprises adding carbon dioxide gas or carbon dioxide solid (dry ice) to a solution comprising a 4-chloro-2-fluoro-3-substituted-phenylboronate, an inert organic solvent, and at least one lithium salt to react the at least one lithium salt with the carbon dioxide gas and form a mixture comprising the 4-chloro-2-fluoro-3-substituted-phenylboronate, the inert organic solvent, and a precipitated solid. The precipitated solid may then be removed from the mixture. The yield of the 4-chloro-2-fluoro-3-substituted-phenylboronate is greater than or equal to about 90%.

DETAILED DESCRIPTION

Methods of isolating a 4-chloro-2-fluoro-3-substituted-phenylboronate, such as PBA-diMe are disclosed. The 4-chloro-2-fluoro-3-substituted-phenylboronate may be synthesized by reacting a solution including a 1-chloro-3-fluoro-2-substituted benzene and an inert organic solvent with an alkyl lithium and an electrophilic boronic acid derivative to form a salinated phenyl boronate solution including the 4-chloro-2-fluoro-3-substituted-phenylboronate, the inert organic solvent, and at least one lithium salt. The 4-chloro-2-fluoro-3-substituted-phenylboronate may be isolated from the at least one lithium salt by exposing the phenyl boronate solution to carbon dioxide ($CO_2$) gas or carbon dioxide solid (dry ice). Following filtration, a desalinated phenyl boronate solution including the 4-chloro-2-fluoro-3-substituted-phenylboronate in the inert organic solvent may be obtained. The desalinated phenyl boronate solution may be used directly in further reactions, such as a Suzuki coupling reaction, to produce additional chemical compounds, such as 6-(4-chloro-2-fluoro-3-substituted-phenyl)-4-aminopicolinates, e.g., methyl-4-amino-3-chloro-6-(4-chloro-2-fluoro-3-substituted-phenyl)pyridine-2-carboxylates.

A reaction scheme for the preparation of a 4-chloro-2-fluoro-3-substituted-phenylboronate from a 1-chloro-3-fluoro-2-substituted benzene is shown below:

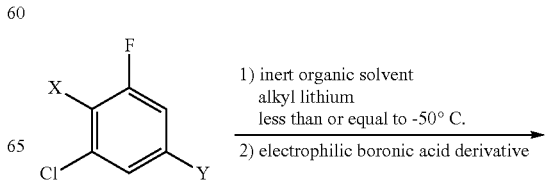

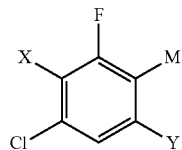

where X is F, OR$_1$, or NR$_2$R$_3$, Y is H or F, each of R$_1$, R$_2$, and R$_3$ is independently a methyl group, an ethyl group, a propyl group, or a butyl group, and M is a boronic acid derivative. The reaction scheme is described in detail below.

An alkyl lithium may be added or introduced to a solution including the 1-chloro-3-fluoro-2-substituted benzene to facilitate a lithiation reaction between the 1-chloro-3-fluoro-2-substituted benzene and the alkyl lithium and form a reaction mixture including a lithiated 1-chloro-3-fluoro-2-substituted benzene. In at least some embodiments, the 1-chloro-3-fluoro-2-substituted benzene is 2-chloro-6-fluoroanisole (2,6-CFA). 1-chloro-3-fluoro-2-substituted benzenes may be produced by conventional techniques, which are not described in detail herein. The alkyl lithium may be any compound including lithium and an alkyl functional group (i.e., of straight chain, branched chain, or cyclic configuration), such as methyl, ethyl, 1-methylethyl, propyl, cyclopropyl, butyl, 1,1-dimethylethyl, cyclobutyl, 1-methylpropyl, or hexyl. By means of non-limiting example, the alkyl lithium may include methyl lithium, n-butyl lithium (n-BuLi), s-butyl lithium, t-butyl lithium, or propyl lithium. In one or more embodiments, the alkyl lithium is n-BuLi. Alkyl lithiums are commercially available from numerous sources, including but not limited to, Sigma-Aldrich Co. (St. Louis, Mo.). In embodiments where the 1-chloro-3-fluoro-2-substituted benzene is 2,6-CFA and the alkyl lithium is n-BuLi, the lithiated 1-chloro-3-fluoro-2-substituted benzene may be 6-chloro-2-fluoro-3-lithioanisole (Li-2,6-CFA).

The lithiation reaction may be conducted in an inert organic solvent in which the 1-chloro-3-fluoro-2-substituted benzene is at least partially soluble. In one or more embodiments, the 1-chloro-3-fluoro-2-substituted benzene is at least substantially dissolved in the inert organic solvent. The inert organic solvent may include, but is not limited to, a C$_5$-C$_8$ hydrocarbon (i.e., of straight-chain, branched, or cyclic configuration), such as a pentane, a hexane, a cyclohexane, an iso-octane, an ether (e.g., diethyl ether, tetrahydrofuran, dioxane, glycol ethers including 1,2-dimethoxyethane), or combinations thereof. In at least some embodiments, the inert organic solvent is 1,2-dimethoxyethane (DME).

At least one molar equivalent of the alkyl lithium may be used relative to the 1-chloro-3-fluoro-2-substituted benzene. The alkyl lithium may be added in a slight excess relative to the 1-chloro-3-fluoro-2-substituted benzene compound, such as from about 1% to about 10% molar excess relative to the 1-chloro-3-fluoro-2-substituted benzene, or from about 2% to about 5% molar excess relative to the 1-chloro-3-fluoro-2-substituted benzene. The lithiation reaction may be conducted under anhydrous conditions, at atmospheric pressure or greater, and at a temperature of less than or equal to about $-30°$ C., preferably less than $-50°$ C., such as less than about $-65°$ C. The reaction mixture may be agitated (e.g., via stirring, ultrasonically agitating, shaking a containment vessel) for a sufficient amount of time to facilitate the deprotonation of the 1-chloro-3-fluoro-2-substituted benzene at a position (C4) between a carbon atom (C3) to which the fluoro substituent is bonded and another carbon atom (C5) to which the Y group is bonded. The lithiation reaction may be conducted under an inert atmosphere, such as under a nitrogen (N$_2$) atmosphere.

An electrophilic boronic acid derivative may be added or introduced to the reaction mixture to react with or contact the lithiated 1-chloro-3-fluoro-2-substituted benzene and form a salinated phenyl boronate solution including a (4-chloro-2-fluoro-3-substituted-phenyl)boronate, the inert organic solvent, and at least one lithium salt, such as lithium methoxide. The electrophilic boronic acid derivative may be a trialkyl borate, such as trimethyl borate (B(OMe)$_3$), triisopropyl borate (B(OiPr)3 or triethyl borate (B(OEt)$_3$). In at least some embodiments, the electrophilic boronic acid derivative is B(OMe)$_3$. In embodiments in which the electrophilic boronic acid derivative is B(OMe)$_3$ and the lithiated 1-chloro-3-fluoro-2-substituted benzene is Li-2,6-CFA, the 4-chloro-2-fluoro-3-substituted-phenylboronate may be dimethyl 4-chloro-2-fluoro-3-methoxyphenylboronate (PBA-diMe). The electrophilic boronic acid derivative may be added slowly, while maintaining a temperature of the reaction mixture of less than or equal to about $-65°$ C. The reaction mixture may be agitated for an amount of time sufficient for the electrophilic boronic acid derivative to react with the lithiated 1-fluoro-2-substituted-3-chlorobenzene. By the end of the reaction the salinated phenyl boronate solution may have a temperature within a range of from about 20° C. to about 25° C. (e.g., ambient temperature).

To isolate the 4-chloro-2-fluoro-3-substituted-phenylboronate, CO$_2$ gas may be added or introduced to the salinated phenyl boronate solution (e.g., bubbling CO$_2$ through the salinated phenyl boronate solution) or adding carbon dioxide solid (dry ice) to react with the at least one lithium salt and form a mixture including precipitated solids, such as lithium methyl carbonate. The precipitated solids may be substantially separated or removed (e.g., via filtering the mixture) to form a desalinated phenyl boronate solution including the 4-chloro-2-fluoro-3-substituted-phenylboronate in the inert organic solvent. In at least some embodiments, the desalinated phenyl boronate solution includes PBA-diMe in DME. The 4-chloro-2-fluoro-3-substituted-phenylboronate may remain in the desalinated phenyl boronate solution and may be used directly in subsequent reactions without additional concentration or drying. Optionally, the desalinated phenyl boronate solution may be desolvated under reduced pressure or by crystallization to isolate the 4-chloro-2-fluoro-3-substituted-phenylboronate as a solid.

The detailed reaction scheme below illustrates a representative conversion of 2,6-CFA to PBA-diMe:

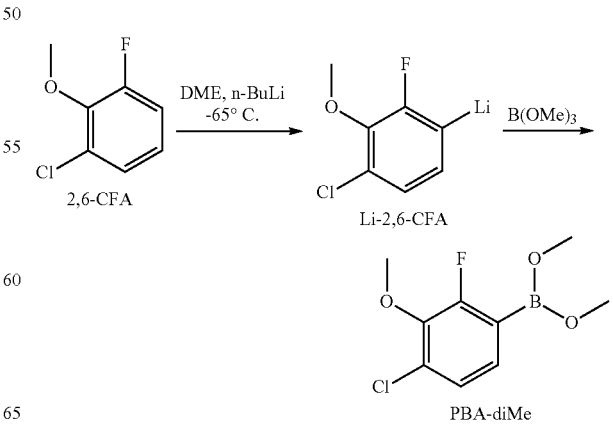

2,6-CFA may be reacted with n-BuLi in anhydrous DME at a temperature of less than or equal to about −65° C. to form the reaction mixture including Li-2,6-CFA. B(OMe)$_3$ may be added or introduced to the reaction mixture where it may react with or contact the Li-2,6,CFA and form the salinated phenyl boronate solution including PBA-diMe, DME, and at least one lithium salt. CO$_2$ may be bubbled through the salinated phenyl boronate solution to react with or contact the at least one lithium salt and form the mixture including lithium methyl carbonate, PBA-diMe, and DME. The mixture may be filtered to substantially remove the lithium methyl carbonate and form the desalinated phenyl boronate solution including PBA-diMe in DME. A yield of the PBA-diMe may be greater than or equal to about 90%, such as greater than or equal to about 95%, or greater than or equal to about 97%.

The desalinated phenyl boronate solution or a 4-chloro-2-fluoro-3-substituted-phenylboronate solid may be utilized in additional chemical reactions, such as a Suzuki coupling reaction. By means of non-limiting example, the desalinated phenyl boronate solution (or the 4-chloro-2-fluoro-3-substituted-phenylboronate solid) may undergo a cross-coupling reaction with methyl 4-acetylamino-3,6-dichloropyridine-2-carboxylate (i.e., acetylated aminopyralid methyl ester-AcAP-Me), to produce or form a methyl 4-acetylamino-3-chloro-6-(4-chloro-2-fluoro-3-substituted-phenyl)pyridine-2-carboxylate, such as methyl 4-acetylamino-3-chloro-6-(4-chloro-2-fluoro-3-methoxyphenyl)pyridine-2-carboxylate (Ac729-Me). The cross-coupling reaction may occur in the presence of a palladium catalyst, a ligand, and a base. In at least some embodiments, the palladium catalyst is palladium (II)acetate (Pd(OAc)$_2$), the base is aqueous potassium carbonate (K$_2$CO$_3$), and the ligand is triphenylphosphine (PPh$_3$). The AcAP-Me may be used as a solid or may be provided in a solvent such as MIBK, MeCN, EtOAc, toluene, water, or combinations thereof. In alternative embodiments, PBA-diMe may be used to produce 2-(4-chloro-2-fluoro-3 methoxyphenyl)-6-amino-4-pyrimidinecarboxylic acid. The coupling partner to PBA-diMe would be methyl 6-acetylamino-2-chloropyrimidine-4-carboxylate or its unprotected version the 6-amino-2-chloropyrimidine-4-carboxylic acid.

The palladium catalyst, the ligand, and the base may be added to a deoxygenated mixture including the AcAP-Me and the desalinated phenyl boronate solution (or the 4-chloro-2-fluoro-3-substituted-phenylboronate solid) to form a coupling reaction mixture. The coupling reaction mixture may be agitated at a temperature within a range of from about 40° C. to about 70° C. for a sufficient amount of time to complete a cross-coupling reaction and form a third multi-phase solution having an organic phase including the 6-(4-chloro-2-fluoro-3-substituted-phenyl)-4-amino picolinate, e.g., methyl-4-amino-3-chloro-6-(4-chloro-2-fluoro-3-substituted-phenyl) pyridine-2-carboxylate. The palladium catalyst may be removed (e.g., by exposing the third multi-phase solution to celite), and the organic phase may be separated or extracted. In embodiments where the coupling reaction mixture includes PBA-diMe and AcAP-Me, a yield of Ac729-Me may be greater than about 85%, such as greater than about 90%, or greater than about 95%.

Using a 4-chloro-2-fluoro-3-substituted-phenylboronate in a coupling reaction with AcAP-Me to produce a 6-(4-chloro-2-fluoro-3-substituted-phenyl)-4-aminopicolinate, e.g., methyl-4-amino-3-chloro-6-(4-chloro-2-fluoro-3-substituted-phenyl)pyridine-2-carboxylate, is desirable as compared to using a (4-chloro-2-fluoro-3-substituted-phenyl)boronic acid (e.g., PBA) or using 4-chloro-2-fluoro-3-substituted-phenylboronate ester (e.g., PBE) because it enables the 6-(4-chloro-2-fluoro-3-substituted-phenyl)-4-aminopicolinate, e.g., methyl-4-amino-3-chloro-6-(4-chloro-2-fluoro-3-substituted-phenyl)pyridine-2-carboxylate, to be produced with fewer unit operations (e.g., operations typically associated with, for example, the formation of PBA or PBE, such as hydrolysis, first phase separation, organic wash, second phase separation, acidification, and extraction may be omitted). Yet, using the salinated phenyl boronate solution including the 4-chloro-2-fluoro-3-substituted-phenylboronate, the inert organic solvent, and the at least one lithium salt in a coupling reaction with AcAP-Me produces methyl-4-acetylamino-3-chloro-6-(4-chloro-2-fluoro-3-substituted-phenyl)pyridine-2-carboxylate in very poor yields (e.g., less than 5%). Without being bound to a particular theory, it is believed that the very poor yields are due to hydrolysis effectuated by the presence of the at least one lithium salt. Favorably, adding or introducing CO$_2$ gas or CO$_2$ solid (dry ice) to the salinated phenyl boronate solution facilitates the removal of the at least one lithium salt, enabling methyl-4-acetylamino-3-chloro-6-(4-chloro-2-fluoro-3-substituted-phenyl)pyridine-2-carboxylate to be produced in good yields (e.g., greater than or equal to 85%) through a coupling reaction between the desalinated phenyl boronate solution and AcAP-Me.

Adding or introducing CO$_2$ gas or CO$_2$ solid (dry ice) to the salinated phenyl boronate solution to isolate the 4-chloro-2-fluoro-3-substituted-phenylboronate in the inert organic solvent also provides the opportunity to recycle or recover the inert organic solvent before any water has been added or introduced to the inert organic solvent. Generally, to be utilized in the lithiation reaction between the 1-chloro-3-fluoro-2-substituted benzene and the alkyl lithium, the inert organic solvent is kept substantially water-free (commonly referred to as being "dry"). Since at least some inert organic solvents, such as DME, are substantially miscible in water, separating the inert organic solvent from water may be difficult and counter-productive. The process of synthesizing a 4-chloro-2-fluoro-3-substituted-phenylboronic acid or a 4-chloro-2-fluoro-3-substituted-phenylboronate ester typically exposes the inert organic solvent to water (e.g., during a hydrolysis of the (4-chloro-2-fluoro-3-substituted-phenyl)boronate via an aqueous base). Conversely, isolating the 4-chloro-2-fluoro-3-substituted-phenylboronate in the inert organic solvent with CO$_2$ gas or CO$_2$ solid (dry ice) and using the desalinated phenyl boronate solution to produce 6-(4-chloro-2-fluoro-3-substituted-phenyl)-4-aminopicolinates, e.g., methyl-4-amino-3-chloro-6-(4-chloro-2-fluoro-3-substituted-phenyl) pyridine-2-carboxylate, may circumvent exposing the inert organic solvent to water, at least enabling a more efficient recycle or reuse of the inert organic solvent for additional lithiation processes.

The following examples serve to explain embodiments of the present disclosure in more detail. These examples are not to be construed as being exhaustive or exclusive as to the scope of this invention.

EXAMPLES

Example 1

Synthesis, Isolation, and Use of PBA-diMe

A solution of 2,6-CFA (15.2 g, 93.5 mmol) in anhydrous DME (118 mL) was prepared in a 500 mL bottle. Molecular sieves were added to remove water, and the water content was measured by Karl Fischer titration to assure water <100 ppm (80 ppm measured). The solution was transferred to a reactor through a septum port and the septum was replaced. A nitrogen pad was started. An agitator was started and set at 270 rpm. A dewar dish under the reactor was filled half full with acetone solvent. Dry ice chunks were slowly added. When the bath solvent was cold more solvent was slowly added so the bath solvent level was above the level of the 2,6-CFA solution in the reactor. The bath was maintained at −76° C. during the experiment by adding dry ice chunks periodically. The 2,6-CFA solution was allowed to cool to −72° C. n-BuLi in hexanes (2.5 M, 41.5 ml) was loaded into a 60 mL plastic syringe and positioned on a syringe pump. The syringe pump was started with an addition rate of 0.7 ml/min. The n-BuLi addition was complete after 64 minutes. The reaction solution was held as −72° C. for 57 minutes. B(OMe)$_3$ (13.1 g, 14.06 mL) was loaded into a 24 mL plastic syringe and positioned on the syringe pump. The agitator was increased to 302 rpm. With the reaction solution at −72° C., the syringe pump was started with an addition rate of 0.4 mL/min. The borate addition was complete after 40 minutes. The reaction solution was left in the cold bath over night at 220 rpm agitation. A total of 153 g of the reaction solution containing PBA-diMe was collected. A GC method with an internal standard was used to quantify the amount of PBA-diMe in solution. A conversion to PBA-diMe of 98% was calculated with 2% of the original unconverted 2,6-CFA also quantified. The PBA-diMe solution was stirred at 18° C. in the reactor. The agitator was started and set to 294 rpm. $CO_2$ gas from a small lecture bottle was slowly bubbled into the solution through a ¼ inch glass tube over 42 minutes. The solution heated to 21° C. A total of 7.2 g (1.5 equivalents) of $CO_2$ gas was added. The mixture was very cloudy with fine white solids. The mixture (153 g) was filtered in a 7.5 cm Buchner funnel using #1 Whatman filter paper and a water aspirator. Fine white solids were removed (lithium methyl carbonate). 3.5 g of hexane was used to rinse the solids. 141 g of filtrate was collected. 3.5 g of dry white solids were collected. The PBA-diMe filtrate solution was place in a 500 mL round bottom flask on a roto-vap fitted with a water aspirator, dry ice trap, and an overhead receiver. The roto-vap was started with the bath at 25° C. The vacuum ranged from 45 mmHg down to 15 mmHg and the final bath temperature was 31° C. After 17 minutes 106.5 g of overhead solvent was collected and 30.1 g of bottoms remained. Analysis of the bottoms by GC gave 59.4% by weight of PBA. The procedure resulted in 97% recovery of PBA. Some of the PBA-diMe filtrate solution was used in a Suzuki coupling reaction. To a 50 mL 3-neck round bottom flask equipped with a condenser, thermocouple temperature probe, magnetic stir bar and $N_2$ inlet was added AcAP-Me (3.0 g, 11.4 mmol). To the round bottom flask was added PPh$_3$ (90 mg, 0.342 mmol) followed by tetrabutylammonum bromide (TBAB, 37 mg, 0.114 mmol). Pd(OAc)$_2$ (26 mg, 0.114 mmol) was added as a solid to the round bottom flask under a nitrogen atmosphere. The solvents, toluene (16.3 mL) and acetonitrile (3.0 mL) were sparged separately with $N_2$ for 30 minutes with stirring then added to the reaction mixture. The reaction mixture was stirred for 5 minutes before adding an aqueous solution of $K_2CO_3$ (22.8%, 17 mL, previously sparged for 30 minutes with $N_2$). The reaction mixture was heated to 65° C. and stirred for 2 hours. After 2 hours the reaction was sampled by GC to determine completion of the reaction. Once the reaction was complete the mixture was transferred to a heated separatory funnel and the phases separated. The organic phase was sampled by GC with an internal standard (valerophenone) to yield Ac729-Me (3.55 g, 81%) with an 89% conversion.

Example 2

Comparative Example 2,6-CFA (144.5 g, 900 mmol) was weighed directly into a 3-neck 2-L round bottom flask equipped with an overhead mechanical stirrer, a thermocouple temperature probe, and a $N_2$ inlet. Anhydrous DME (1125 mL) was added to the round bottom flask. The reaction was cooled to −78° C. with a dry ice/acetone bath. Once the reaction reached about −77° C. n-BuLi (425 mL, 1035 mmol, 2.5M in Hexanes) was slowly added dropwise using a syringe pump over a 1 hour period. The highest temperature reached during addition was −68.8° C. After the addition of n-BuLi was complete, the reaction was left to stir for 1 hour at −73.5° C. After 1 hour, B(OMe)$_3$ (10.5 mL, 93.42 mmol) was added dropwise using an addition funnel over about a 1 hour period. The highest temperature reached during the addition was −65.6° C. After the addition of B(OMe)$_3$ was complete, the reaction mixture was warmed to room temperature overnight. Once the reaction mixture reached room temperature, the reaction mixture was left to stir an additional 1 hour at that temperature (~20.4° C.). A PBA-diMe solution (115.74 g) was removed for reactions and stability studies. The PBA-diMe was analyzed by GC using an internal standard (valerophenone) to give a 17.07% by weight of PBE (13.02% by weight of PBA). The procedure resulted in 95% recovery of PBA. Some of the PBA-diMe solution was used in a Suzuki Coupling reaction. To a 50 mL 3-neck round bottom flask equipped with condenser, thermocouple temperature probe, magnetic stir bar and $N_2$ inlet was added AcAP-Me (3.0 g, 11.4 mmol). To the round bottom flask was added PPh$_3$ (90 mg, 0.342 mmol) followed by TBAB (37 mg, 0.114 mmol). Pd(OAc)$_2$ (26 mg, 0.114 mmol) was added as a solid to the round bottom flask under a $N_2$ atmosphere. MeCN (19.0 mL) was sparged separately with $N_2$ for 30 min with stirring then added to the round bottom flask. The PBA-diMe solution (17.07 wt %, 14.82 mmol) was sparged with $N_2$ for 30 min with stirring then added to the reaction mixture. The reaction mixture was stirred for 5 min before adding an aqueous solution of $K_2CO_3$ (22.8%, 17 mL, previously sparged for 30 min with nitrogen). The reaction mixture was heated to 65° C. and stirred for 2 hours. After 2 hours, the reaction was sampled by GC to determine completion of the reaction. GC showed very little product (<5%). GC also showed complete consumption of AcAP-Me (possibly due to hydrolysis).

While the invention may be susceptible to various modifications and alternative forms, specific embodiments have been described by way of example in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of using a 4-chloro-2-fluoro-3-substituted-phenylboronate comprising reacting the 4-chloro-2-fluoro-3-substituted-phenylboronate with methyl 4-acetylamino-3,6-dichloropyridine-2-carboxylate in a medium consisting of a palladium catalyst, a ligand, tetrabutylammonum bromide (TBAB), a base, and at least one solvent to produce a methyl-4-acetylamino-3-chloro-6-(4-chloro-2-fluoro-3-substituted-phenyl)pyridine-2-carboxylate.

2. The method of claim 1, wherein the at least one solvent is selected from 4-methylpentan-2-one, acetonitrile, toluene, ethyl acetate, or water.

3. The method of claim 1, wherein reacting the 4-chloro-2-fluoro-3-substituted-phenylboronate with the methyl 4-acetylamino-3,6-dichloropyridine-2-carboxylate to produce the methyl-4-acetylamino-3-chloro-6-(4-chloro-2-fluoro-3-substituted-phenyl)pyridine-2-carboxylate comprises reacting dimethyl 4-chloro-2-fluoro-3-methoxyphenylboronate with the methyl 4-acetylamino-3,6-dichloropyridine-2-carboxylate to produce methyl 4-acetylamino-3-chloro-6-(4-chloro-2-fluoro-methoxyphenyl)pyridine-2-carboxylate.

4. The method of claim 3, wherein reacting the dimethyl 4-chloro-2-fluoro-3-methoxyphenylboronate with the methyl 4-acetylamino-3,6-dichloropyridine-2-carboxylate to produce the methyl 4-acetylamino-3-chloro-6-(4-chloro-2-fluoro-methoxyphenyl)pyridine-2-carboxylate comprises obtaining a yield of the methyl 4-acetylamino-3-chloro-6-(4-chloro-2-fluoro-methoxyphenyl)pyridine-2-carboxylate of greater than or equal to about 85%.

5. The method of claim 1, wherein reacting the 4-chloro-2-fluoro-3-substituted-phenylboronate with the methyl 4-acetylamino-3,6-dichloropyridine-2-carboxylate to produce the methyl-4-acetylamino-3-chloro-6-(4-chloro-2-fluoro-3-substituted-phenyl)pyridine-2-carboxylate comprises:
- adding a palladium catalyst, a ligand, tetrabutylammonum bromide (TBAB), and a base to a deoxygenated mixture comprising the (4-chloro-2-fluoro-3-substituted-phenyl)boronate, methyl 4-acetylamino-3,6-dichloro pyridine-carboxylate, and at least one solvent to form a coupling reaction mixture;
- agitating the coupling reaction mixture at a temperature within a range of from about 40° C. to about 70° C. to form a multi-phase solution comprising an aqueous phase and an organic phase, the organic phase comprising the methyl-4-acetylamino-3-chloro-6-(4-chloro-2-fluoro-3-substituted-phenyl)pyridine-2-carboxylate; and
- separating the organic phase from the aqueous phase.

* * * * *